(12) United States Patent
Bertrand et al.

(10) Patent No.: US 11,208,860 B2
(45) Date of Patent: Dec. 28, 2021

(54) GAS-EXTRACTION DEVICE AND ASSOCIATED ANALYSIS ASSEMBLY AND METHOD

(71) Applicant: Geoservices Equipements, Roissy-en-France (FR)

(72) Inventors: Paul Bertrand, Roissy-en-France (FR); Patrick Banik, Roissy-en-France (FR); Jerome Breviere, Roissy-en-France (FR); Nassim Bentamy, Roissy-en-France (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 381 days.

(21) Appl. No.: 15/772,188

(22) PCT Filed: Oct. 27, 2016

(86) PCT No.: PCT/EP2016/001787
§ 371 (c)(1),
(2) Date: Apr. 30, 2018

(87) PCT Pub. No.: WO2017/076490
PCT Pub. Date: May 11, 2017

(65) Prior Publication Data
US 2018/0320463 A1  Nov. 8, 2018

(30) Foreign Application Priority Data

Nov. 5, 2015  (EP) ..................................... 15290283

(51) Int. Cl.
*B01D 19/00* (2006.01)
*E21B 21/06* (2006.01)
(Continued)

(52) U.S. Cl.
CPC ........ *E21B 21/067* (2013.01); *B01D 19/0052* (2013.01); *E21B 21/08* (2013.01); *E21B 49/005* (2013.01); *G01N 33/2823* (2013.01)

(58) Field of Classification Search
CPC ... B01D 19/0052; E21B 21/067; E21B 21/08; E21B 49/005; G01N 33/2823
See application file for complete search history.

(56) References Cited

U.S. PATENT DOCUMENTS 2,489,180 A * 11/1949 Hayward ................ E21B 21/01
73/152.04
2,923,151 A * 2/1960 Engle .................... G01N 1/2211
73/152.04
(Continued)

FOREIGN PATENT DOCUMENTS

WO  WO2006114512 A1  11/2006

OTHER PUBLICATIONS

Extended European Search Report issued in the related EP Application 15290283.9, dated Apr. 13, 2016 (7 pages).
(Continued)

*Primary Examiner* — Cabrena Holecek (57) ABSTRACT

Gas-extraction device (152) for extracting at least one gas contained in a drilling mud, the device comprising: —an enclosure (162), —an equipment (164) for supplying the drilling mud to the enclosure (162), —an equipment (170) for introducing a carrier gas into the enclosure (62; 162), wherein the device comprises a flow regulator (204) able to regulate the flow rate of a gas flow containing at least carrier gas, and a pressure controller situated downstream of the enclosure (162) configured for locally setting a pressure lower than the pressure of the enclosure (162), wherein the flow, regulator (204) is interposed between the pressure controller and the enclosure (162).

20 Claims, 6 Drawing Sheets

(51) Int. Cl.
*E21B 21/08* (2006.01)
*E21B 49/00* (2006.01)
*G01N 33/28* (2006.01)

(56) References Cited

U.S. PATENT DOCUMENTS

| | | | |
|---|---|---|---|
| 4,635,735 A * | 1/1987 | Crownover | E21B 21/067 |
| | | | 175/42 |
| 4,887,464 A * | 12/1989 | Tannenbaum | E21B 49/005 |
| | | | 73/152.04 |
| 7,794,527 B2 | 9/2010 | Sterner | |
| 2006/0224333 A1 * | 10/2006 | Frechin | G01N 33/2823 |
| | | | 702/24 |
| 2006/0254421 A1 | 11/2006 | Boone | |
| 2007/0292612 A1 * | 12/2007 | Ueno | C23C 16/52 |
| | | | 427/248.1 |
| 2009/0199618 A1 | 8/2009 | Evrard | |

OTHER PUBLICATIONS

International Search Report and Written Opinion issued in the related PCT application PCT/EP2016/001787, dated Feb. 16, 2017 (12 pages).

Office Action issued in the related EP Application 15290283.9, dated Dec. 8, 2017 (5 pages).

* cited by examiner

GAS-EXTRACTION DEVICE AND ASSOCIATED ANALYSIS ASSEMBLY AND METHOD

The present disclosure concerns a gas-extraction device for extracting at least one gas contained in a drilling mud, the device comprising an enclosure, an equipment for supplying the drilling mud to the enclosure and an equipment for introducing a carrier gas into the enclosure.

When an oil well or other effluent well (especially gas, vapour, water) is drilled, it is known to carry out an analysis of the gaseous compounds contained in the drilling muds emerging from the well. This analysis enables the geological succession of the formations traversed during drilling to be reconstituted and is involved in the determination of the possibilities of working the fluid deposits encountered.

This analysis, which is carried out continuously, comprises two main stages. The first stage consists in extracting the gases conveyed by the mud (for example, hydrocarbon compounds, carbon dioxide, hydrogen sulfide, etc.). The second stage consists in qualifying and quantifying the gases extracted.

In the first stage, gas-extraction devices with mechanical agitation of the above-mentioned type are often used. The gases extracted from the mud, which are mixed with the carrier gas introduced into the enclosure, are conveyed by suction by means of a gas pump to an analyzer which enables the extracted gases to be quantified.

The gas pump, which is generally a vacuum pump, is a source of unpredicted maintenance. Such maintenance can be difficult to carry out in the vicinity of a well, at a location which may not be very accessible. Consequently, the gas pump rate can decrease without any sign for the user and the gas flow rate may be modified. Thus, the gas analysis will therefore be disrupted and, sometimes, has to be interrupted in order to replace the pump.

Additionally, gas pumps are expensive and a very few models are certified to be located in an explosive zone. As a consequence, the gas pump is generally installed in the mud logging unit, close to the analyzer. This leads to the use of long gas lines, which may have an unpredictable behavior regarding hydrocarbons adsorption during transportation for example.

The disclosure provides a device for extracting at least one gas contained in a drilling mud with enhanced reliability of the extraction and analysis of the gas, and lower maintenance.

The disclosure relates to a gas-extraction device for extracting gas contained in a drilling mud, comprising an enclosure, an equipment for supplying the drilling mud to the enclosure and an equipment for introducing a carrier gas into the enclosure. The device also comprises a flow regulator to regulate the flow rate of a gas flow containing carrier gas, and a pressure controller for locally setting a pressure distinct from the pressure of the enclosure. The flow regulator is interposed between the pressure controller and the enclosure and the pressure controller is set so that the one of the pressure controller and enclosure which is situated upstream from the flow regulator has a higher pressure than the one situated downstream.

In particular, the pressure controller is situated downstream of the enclosure and setting a lower pressure than the pressure of the enclosure. It may be a Venturi pump.

The gas-extraction device according to the disclosure may comprise one or more of the following features, taken in isolation or according to any technically possible combination:

the gas-extraction device comprises a gas analyzer for analyzing the gas, which is connected to the enclosure via a gas-extraction pipe of the gas-extraction device, the gas analyzer is directly connected to the enclosure,
the gas analyzer comprises one of the following analyzers:
  a spectrometer, such as an infrared spectrometer, and/or
  a flame ionization detector chromatograph (FID), and/or
  a thermal conductivity detector chromatograph (TCD), and/or
  a gas chromatography system connected to a mass spectrometer (GC-MS),
the pressure controller comprises a pressurized gas source upstream of the enclosure and able to feed the enclosure with carrier gas,
the pressurized gas source is a source of compressed air from atmosphere,
the pressure analyzer, such as the Venturi vacuum pump is situated downstream of the gas analyzer,
the flow regulator is a sonic nozzle,
the gas-extraction device comprises a tank for receiving the drilling mud, the enclosure being positioned in the tank, and the gas extraction device comprises a level control unit for regulating the level of the mud in the enclosure,
the enclosure is positioned on the upper portion of the tank, the level control unit comprising a floating device, the floating device being able to float on the drilling mud, the floating device moving vertically upwards and downwards through a guiding equipment for guiding the floating device, the enclosure being mounted on the floating device,
the level control unit comprises a detector able to detect a drilling mud level around the enclosure and a level adjusting system, coupled with the detector and configured to raise or to lower the enclosure according to an indicator given by the detector,
the gas extraction pipe has a length inferior to 10 meters,
the flow regulator is configured to regulate the gas flow introduced into the enclosure or exiting the enclosure at a constant value, and
the detector is a pressure measurement apparatus or a level sensor.

The disclosure also relates to a method for extracting at least one gas contained in a drilling mud, the method comprising:
  providing a gas-extraction device as defined above,
  feeding the enclosure with drilling mud,
  providing carrier gas in the enclosure and forming a flow of carrier gas and gas extracted from the drilling fluid situated in the enclosure with the pressure controller and the flow regulator.

The method according to the disclosure may comprise the following feature:
  delivering the flow to the gas analyzer and analyzing the gas extracted from the drilling fluid with the gas analyzer.

Other aspects and advantages of the disclosure will appear upon reading the following description, given by way of example and made in reference to the appended drawings, wherein.

Throughout the following, the terms "upstream" and "downstream" are to be understood in relation to the direction of flow of a fluid in a pipe.

An analysis assembly according to the disclosure is used, for example, in an installation 10 for drilling an oil production well.

Figure 1:
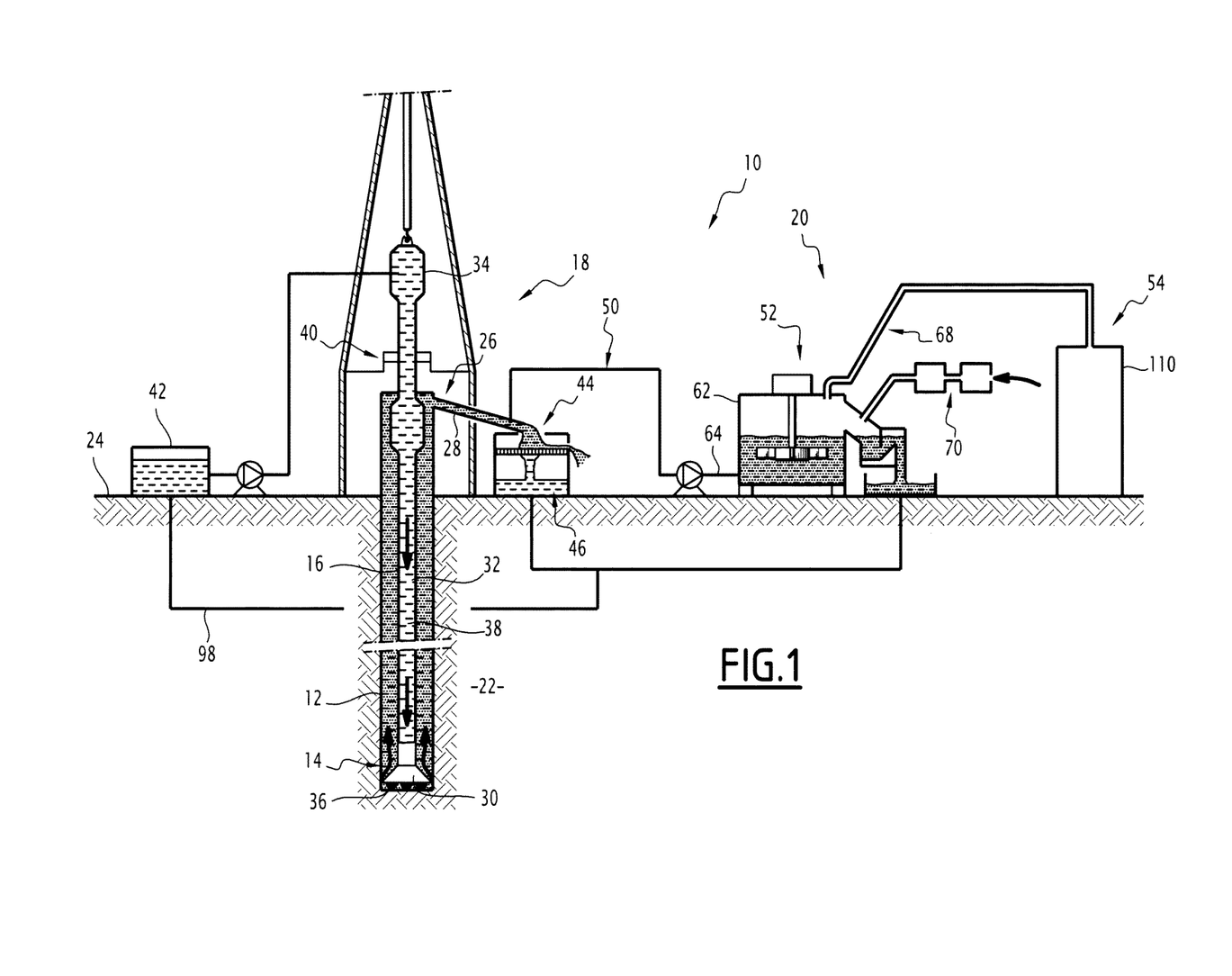
FIG. 1 is a diagrammatic view in vertical section of a drilling installation provided with a first device according to the disclosure.

As illustrated in FIG. 1, the installation 10 comprises a drilling duct 12 in a cavity 14 bored by a rotary drilling tool 16, a surface installation 18, and an analysis assembly 20 according to the disclosure.

The drilling duct 12 is located in the cavity 14 bored in the sub-soil 22 by the rotary drilling tool 16. The duct 12 comprises, at the surface 24, a well head 26 provided with a draining pipe 28.

The drilling tool 16 comprises a drilling head 30, a drilling string 32, and a head 34 for the injection of liquid.

The drilling head 30 comprises drill bits 36 for boring through the rocks of the sub-soil 22. The drilling head 30 is mounted on the lower portion of the drilling string 32 and is positioned at the bottom of the drilling duct 12.

The drilling string 32 comprises a set of hollow drilling tubes. These tubes delimit an internal space 38 which enables a liquid to be supplied from the surface 24 to the drilling head 30. For that purpose, the head 34 for injecting liquid is screwed onto the upper portion of the drilling string 32.

The surface installation 18 comprises a support 40 for supporting and rotatably driving the drilling tool 16, injector 42 for injecting the drilling liquid, and a vibrating screen 44.

The injector 42 is connected hydraulically to the injection head 34 in order to introduce a liquid and to cause it to flow in the internal space 38 of the drilling string 32.

The vibrating screen 44 collects the liquid which is charged with drilling residues and which is discharged from the draining pipe 28 in a container 46, and separates the liquid from the solid drilling residues.

Figure 2:
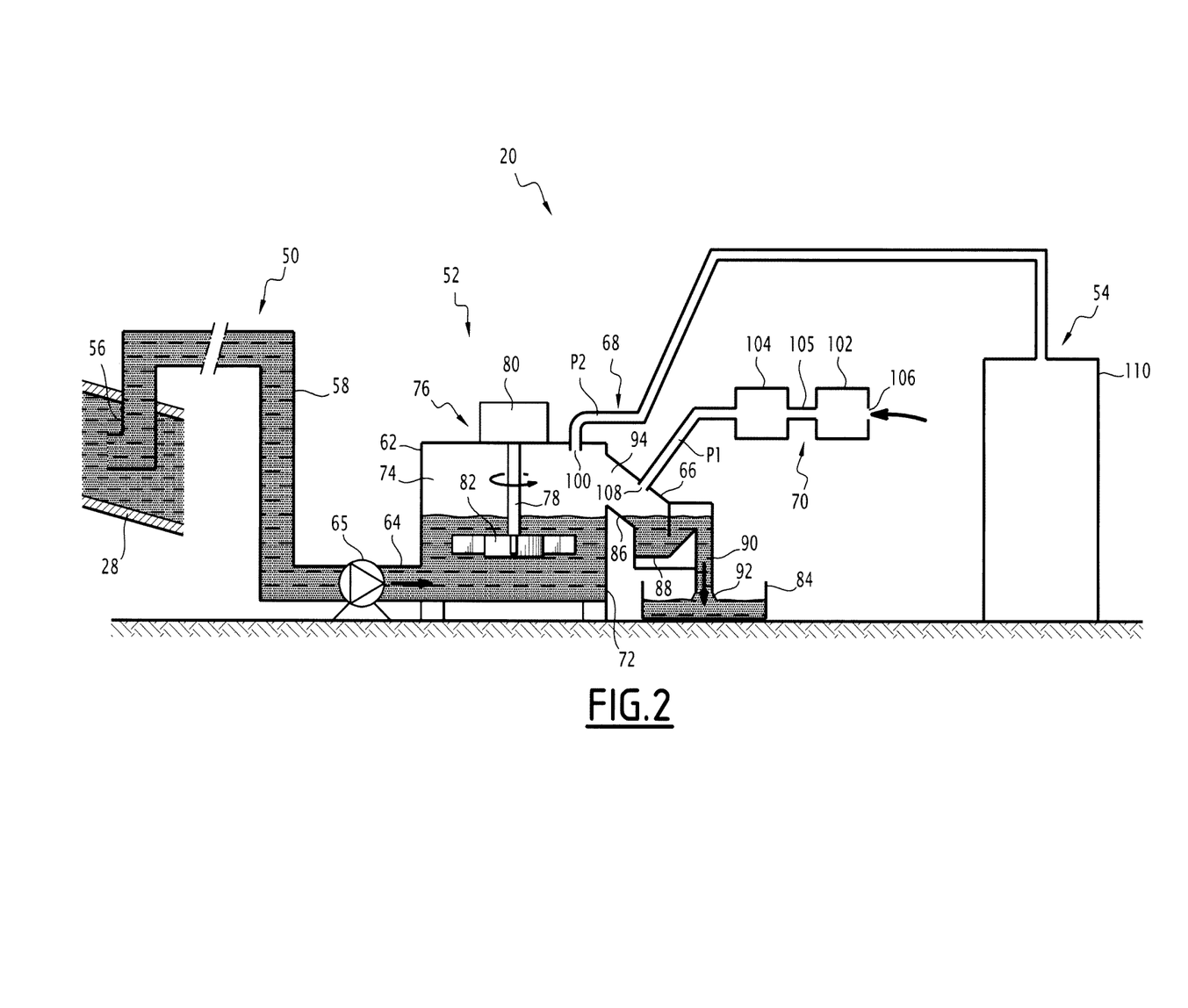
FIG. 2 is a diagrammatic view in vertical section of the analysis assembly of the drilling installation of FIG. 1.

In the example of FIG. 2, the analysis assembly 20 comprises a mud sampler 50 tapped into the draining pipe 28 and a gas-extraction device 52.

The mud sampler 50 comprises a liquid-sampling head 56 located in a projecting manner in the draining pipe 28 and a connecting tube 58.

The gas-extraction device 52 comprises a gas analyzer 54 for analyzing the extracted gases, an enclosure 62, an equipment 64 for supplying the drilling mud to the enclosure, a discharge pipe 66 for conveying the mud from the enclosure 62 to the gas analyzer 54, a gas-extraction pipe 68 and an equipment 70 for introducing a carrier gas into the enclosure 62.

The enclosure 62 comprises a sealed container, the internal volume of which is, for example, from 0.04 liter to 30 liters. The enclosure 62 comprises a lower portion 72 in which the mud circulates and an upper portion 74 which has a gaseous blanket. The enclosure 62 is also provided with agitating unit 76 comprising an agitator 78 mounted in a projecting manner in the enclosure 62 and rotatably driven by a motor 80 mounted on the upper portion 74 of the enclosure 62. The agitator 78 comprises an agitating moving body 82 immersed in the mud.

The equipment 64 for supplying mud is a supply pipe which is connected to the connecting tube 58 for receiving the drilling mud and is connected to an inlet opening provided in the lower portion 72 of the enclosure 62. The supply pipe 64 comprises a peristaltic pump 65, the flow rate of which is adjustable, to feed the enclosure 62.

This supply pipe 64 may be provided with a heater (not shown) for heating the mud in order to bring the temperature of the mud to values of from 25 to 120° C., preferably from 60 to 90° C.

The discharge pipe 66 extends between an overflow passage provided in the upper portion 74 of the enclosure 62, and a retaining receptacle 84 which is to receive the muds discharged from the gas-extraction device 52.

The discharge pipe 66 comprises, in succession, a downwardly inclined upstream portion 86, which forms an angle of approximately 45° with the horizontal, a siphonforming bent portion 88, and a substantially vertical downstream portion 90 which is open at its lower end 92 facing the receptacle 84, above the level of the liquid contained in the receptacle 84.

The mud introduced into the enclosure 62 via the supply pipe 64 is discharged by overflowing into the discharge pipe 66 via the overflow passage. In addition, some of the mud discharged dwells temporarily in the siphon 88 of the discharge pipe 66, which prevents gas from entering the upper portion 74 of the enclosure 62 by way of the lower end 92 of the discharge pipe 66. The introduction of gas into the enclosure 62 is therefore effected purely by the equipment 70 for introducing a carrier gas.

The mud collected in the retaining receptacle 84 and in the container 46 is recycled to the injector 42 by way of a pipe 98 for recirculating mud.

The gas-extraction pipe 68 extends between an extraction opening 100, provided in the upper portion 74 of the enclosure 62, and the gas analyzer 54. The gas-extraction pipe 68 is directly connected to the gas analyzer 54. In particular, according to the disclosure, the gas-extraction pipe 68 is deprived of apparatus such as a pump adapted to suction the gas contained into the enclosure 62 for releasing it to the gas analyzer 54. The maintenance of the gas-extraction pipe is therefore extremely simple.

The gas-extraction pipe 68 connects the enclosure 62, located in the vicinity of the well head 26, in an explosive region, to the gas analyzer 54 located at a distance from the well head 26, in a non-explosive region, for example, in a pressurized cabin. Alternatively, the gas analyzer 54 is situated in the explosive region. The gas-extraction pipe 68 can be manufactured from a polymeric material, especially polyethylene, and has, for example, a length ranging from 5 meters to 500 meters if the gas analyzer 54 is situated in the cabin or from 0 to 5 meters when the gas analyzer 54 is-situated in the explosive region. Providing the gas analyzer 54 in the explosive region enables to decrease the transport time of the gas and to obtain real-time measurements.

The equipment 70 for introducing a carrier gas into the enclosure 62 may comprise a pressure controller, including a pressurized gas source 102, and a flow regulator 104. However, the equipment 70 may comprise a simple conduit for introducing air from the atmosphere or a source of non-pressurized gas while the pressure controller and the flow regulator are situated downstream of the enclosure (as disclosed in FIG. 6). The installation (at the exception of the pressure controller and flow regulator) and in particular the extractor and analyzer as disclosed in connection with FIGS. 1 and 2 may still be used with such a configuration of the pressure controller and flow regulator.

In this embodiment, the pressurized gas source 102 is adapted to feed the enclosure 62. In the illustrated example, the pressurized gas source 102 comprises an air intake 106 for retrieving the air from the atmosphere surrounding the installation, at atmospheric pressure, and a compressor for pressurizing it. It also comprises a link organ 105 for delivering the pressurized gas. This link organ 105 advantageously comprises a check valve, not shown, to prevent the circulation of gases in the link organ towards the pressurized gas source 102.

The link organ 105 is connected to the flow regulator 104. The flow regulator 104 is configured to expand the gas for introducing a carrier gas in the enclosure 62 at a pressure which is substantially equals to the atmospheric pressure. The atmospheric pressure is approximately comprised between 0.9 bars and 1.5 bars.

The flow regulator 104 opens in an injection passage 108 situated on the upper portion 74 of the enclosure 62.

The flow regulator 104 is configured to regulate the gas flow, consisting of the carrier gas, introduced into the enclosure at an expected constant flow rate. The rate of the gas flow introduced into the enclosure depends on the size of the enclosure 62. Usually, the gas flow rate is comprised between 0.1 L/min and 5 L/min. The flow regulator 104 is, for example, a flow restrictor such as a sonic nozzle or a capillary tube.

The gas analyzer 54 for analyzing the extracted gases comprises instrumentation 110 which enables one or more extracted gases to be detected and quantified.

The instrumentation 110 may comprise, for example, apparatus for spectroscopic analysis, such as infrared detection, FID (flame ionization detector) chromatographs, or also TCD (thermal conductivity detector) chromatographs. It may also comprise a gas chromatography system connected to a mass spectrometer, this system having the abbreviation GC-MS. The instrumentation may comprise one or several of the above-mentioned apparatus, in order to detect molecules of interest, such as hydrocarbons in the extracted gas. The detection and simultaneous quantification of a plurality of gases is possible.

The operation of the analysis assembly 10 according to the disclosure, during the drilling of a well, will now be described by way of example with reference to FIG. 1.

In order to carry out a drilling operation, the drilling tool 16 is rotatably driven by the support 40. A drilling liquid is introduced into the internal space 38 of the drilling string 32 by the injector 42. This liquid descends to the drilling head 30 and passes into the drilling duct 12 through the drilling head 30. The liquid cools and lubricates the drill bits 36. The liquid then collects the solid debris resulting from the drilling operation and goes back up via the annular space defined between the drilling string 32 and the walls of the drilling duct 12, and is then discharged by way of the draining pipe 28.

Referring to FIG. 2, the pump 65 is then activated in order to sample continuously a predetermined fraction of the drilling mud flowing in the pipe 28.

This mud fraction is conveyed to the enclosure 62 via the supply pipe 64.

In this example, the carrier gas is air surrounding the installation, at the atmospheric pressure. It is conveyed in the enclosure. When the installation is the one disclosed in FIGS. 1 and 2, the gas is pressurized in the pressurized gas source 102. The flow rate of the carrier gas delivered by the pressurized gas source 102 is regulated by the flow regulator 104 which pushes the carrier gas at a constant flow rate into the upper portion 74 of the enclosure 62 via the injection passage 108.

The agitator 78 is rotatably driven by the motor 80 and agitates the mud in the lower portion 72 of the enclosure 62 in order to bring about the extraction of the gases contained in that drilling mud, and also the mixing of the extracted gases with the carrier gas pushed in via the injection passage 108.

The carrier gas introduced into the enclosure 62 by the equipment 70 mixes with the extracted gases. The mixture is exits, in this case pushed out, from the enclosure 62 via the extraction opening 100. The link organ 105 prevents the gas mixture from circulating from the enclosure 62 to the equipment 70.

So, under the effect of the pushing due to the introduction of the carrier gas, the gas mixture is conveyed via the gas-extraction pipe 68 to the gas analyzer 54 where it is qualified and quantified by the instrumentation 110.

As shown on FIG. 2, reference P1 refers to the pressure of the carrier gas introduced in the enclosure 62 and P2 refers to the pressure of the mixture pushed out from the enclosure 62 to the gas analyzer 54 thought the gas-extraction pipe 68.

The pressure drop along the gas-extraction pipe 68 is negligible since the pressure of the carrier gas introduced in the enclosure 62 is regulated in order to be constant and since the single air outlet of the enclosure 62 is the extraction opening 100 which is directly connected to the gas analyzer 54 without any vacuum pump or regulator. Therefore, P1 is substantially equal to P2.

Moreover, even if the pressure of the carrier gas delivered by the pressurized gas source varies, the pressure downstream to the flow regulator does not change. In terms of maintenance, the pressurized gas source does not need to be monitored accurately.

This gas-extraction device 52 allows, by simple and inexpensive means, the extraction of the mixture from the enclosure 62 and its transport to the gas analyzer 54 without using any device necessitating maintenance, such as a mechanical pump, in particular between the extraction opening 100 of the enclosure 62 and the gas analyzer 54.

Since the equipment 70 for introducing the carrier gas is simple, and since the enclosure 62 is connected to the equipment 70 solely by the gas-extraction pipe 68, the maintenance is considerably reduced. Furthermore, this increases the productivity and safety of the drilling operation.

Finally, the drilling mud level in the enclosure 62 remains constant since the pump 65 continuously delivers drilling mud which is discharged by overflowing into the discharge pipe 66. This allows a constant volume of gas mixture to be sent to the gas analyzer 54 and, as a consequence, allows performing a more accurate gas analysis.

Figure 3:
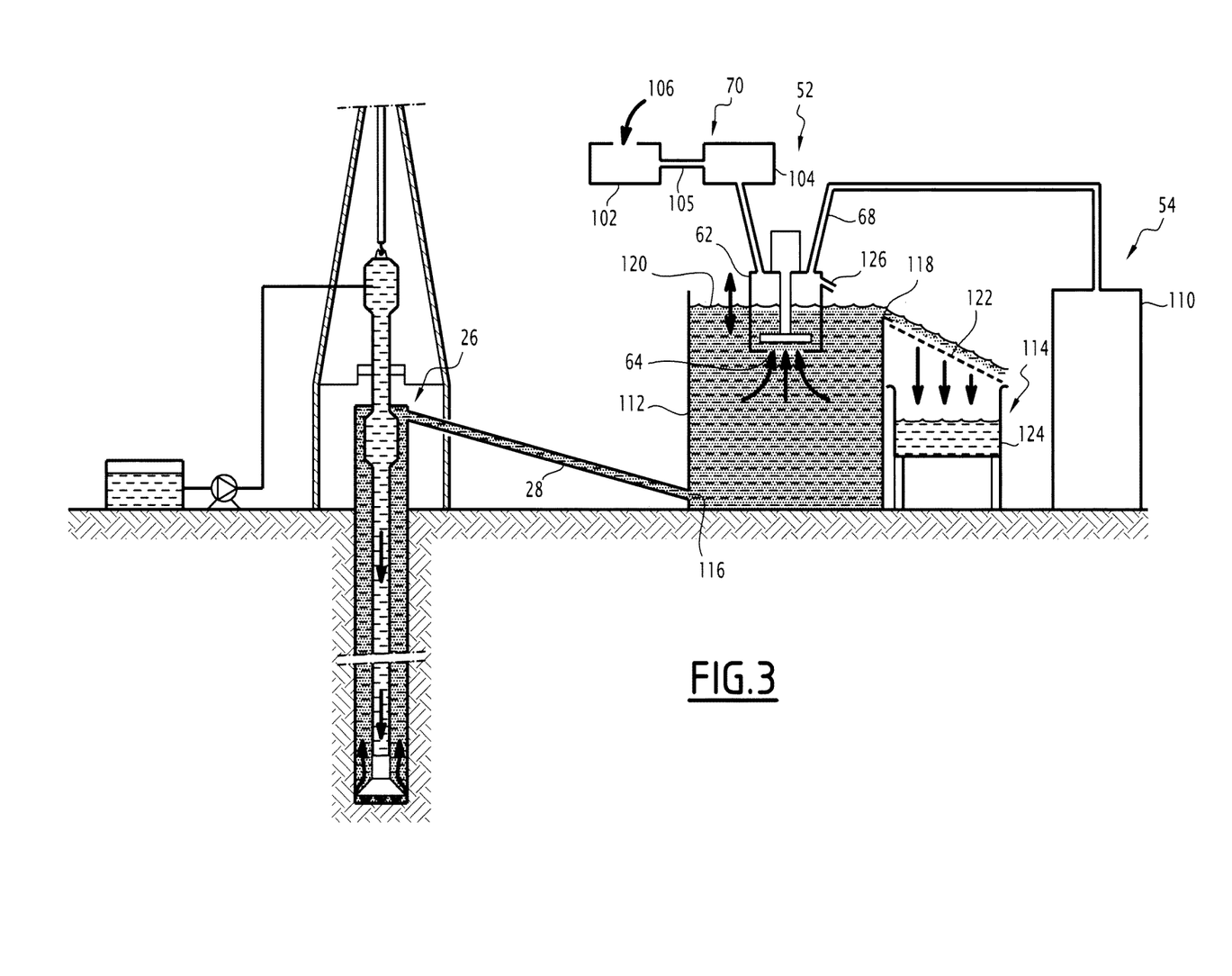
FIG. 3 is a diagrammatic view in vertical section of a drilling installation provided with a second device according to the disclosure.

FIG. 3 illustrates a second, embodiment of a gas-extraction device according to the disclosure. This embodiment is disclosed in connection with a pressure controller upstream of the enclosure but may also be implemented with a pressure controller downstream of the enclosure, as the one of FIG. 6.

Unlike the first embodiment described above, the gas-extraction device 52 comprises a liquid-receiving tank 112 and a waste equipment 114.

The tank 112 comprises a feed opening 116 for receiving the drilling mud and an overflow 118.

The feed opening 116 is directly connected to the draining pipe 28, is deprived of any means such as a pump and feeds the tank 112 up to a level 120.

The overflow 118 is a channel inclined downwards, situated under the level 120 and allows the discharge of the drilling mud onto the waste equipment 114. It comprises a vibrating screen 122 and a container 124 to collect the drilling mud.

In this embodiment, the enclosure 62 is adapted to float on the drilling mud. It comprises the same equipment as in the embodiment of FIG. 2, in particular a lower portion in which the mud circulates, an upper portion which has a gaseous blanket and agitating unit. Moreover, the enclosure 62 comprises mud drainage nozzle 126.

Unlike the embodiment of FIG. 2, the enclosure 62 is filled in with drilling mud through a lower opening 64 defined in the enclosure 62. The lower opening is situated under the agitating unit.

The drilling mud spontaneously enters the enclosure 62 without being pumped, which avoids the use of a pump upwards of the enclosure 62. The maintenance of the second analysis assembly according to the disclosure is further simplified.

The mud drainage nozzle 126, positioned on the side of the enclosure 62 and above the agitator, is able to allow the discharge of the drilling mud into the tank 112.

Figure 4:
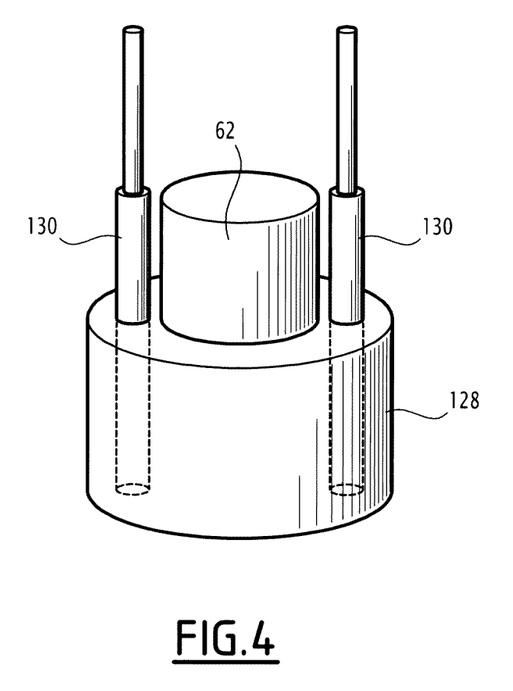
FIG. 4 is a perspective view of the enclosure used in the drilling installation of FIG. 3.

FIG. 4 illustrates the enclosure 62 of FIG. 3 which is mounted on a floating device 128 able to float on the drilling mud. The floating device 128, which is for example a ballast, moves vertically upwards and downwards through an guiding equipment 130 which is, for example, vertical guide rods. Instead of vertical guide rods, the guiding equipment may comprise at least a shaft with rotating bearings at each of its ends.

The guiding equipment 130 comprises, as an example, two parallel guide rods in which the floating device 128 is inserted and fitted to the bottom of the tank 112.

Thus, the enclosure 62 is able to move vertically to follow the current drilling mud level. As a consequence, assuming that the tank 112 is partially filled, the quantity of drilling fluid inside the enclosure 62 is always the same.

The equipment 70 for introducing carrier gas in the enclosure 62 is furthermore identical to the one described above.

The operation of the second analysis assembly according to the disclosure is similar to that of the first assembly except that the drilling mud spontaneously enters the enclosure 62 without being pumped.

Figure 5:
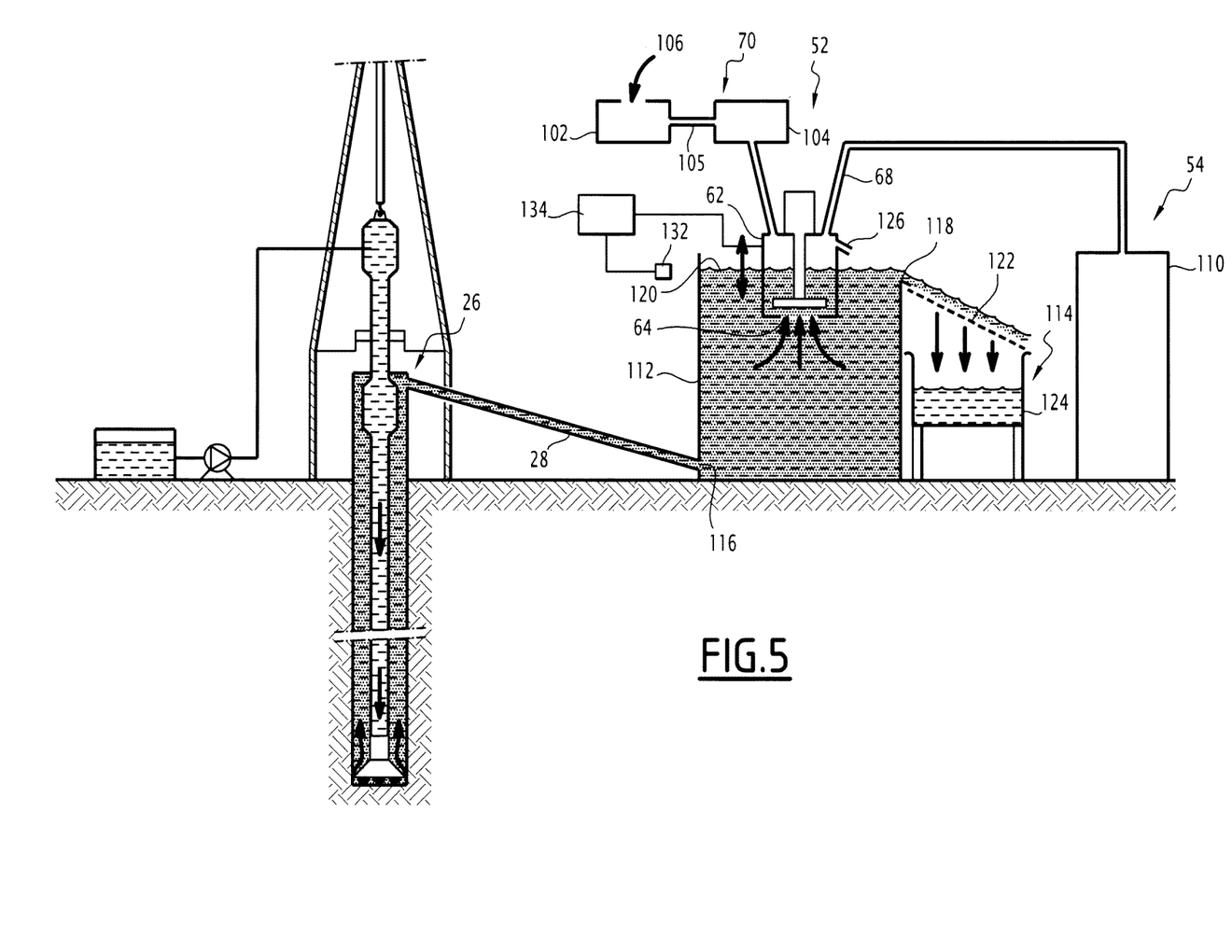
FIG. 5 is a diagrammatic view in vertical section of a drilling installation provided with a third device according to the disclosure.

According to a third embodiment illustrated on FIG. 5, the enclosure 62 is not able to float on the drilling mud and comprises a detector 132 able to detect a drilling mud level around the enclosure 62 and a level system 134.

Figure 6:
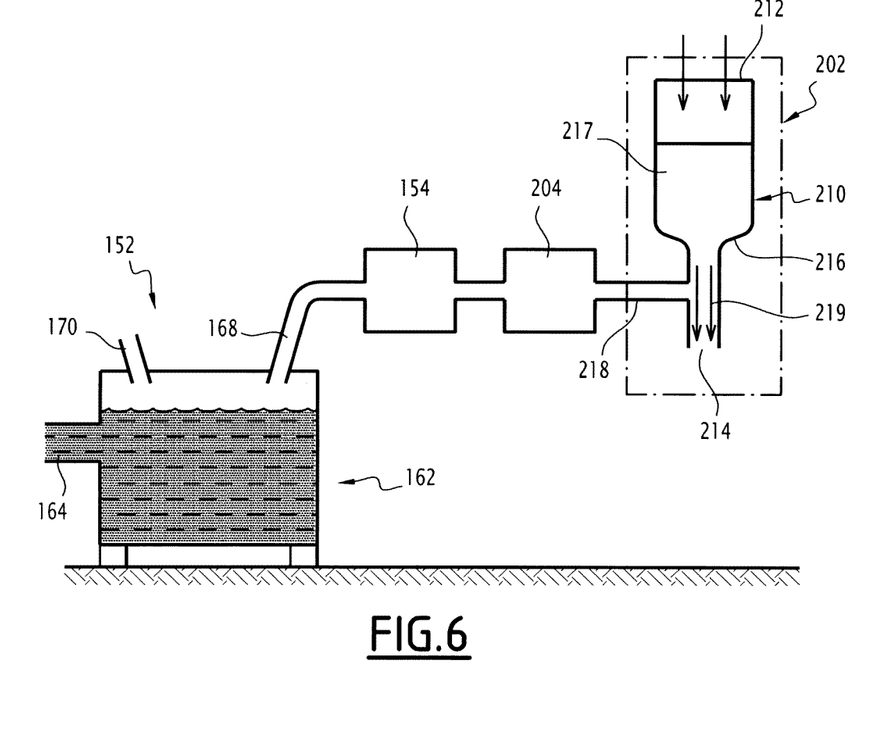
FIG. 6 is a schematic functional diagram of a device according to another embodiment of the disclosure.

As well as the second embodiment, the third embodiment is disclosed in connection with a pressure controller upstream of the enclosure but may also be implemented with a pressure controller downstream of the enclosure, as disclosed in the embodiment of FIG. 6.

The detector 132 is, for example, a pneumatic system based on differential pressure measurement for detecting a rise or a fall of the drilling mud level in the tank 112, such as the one disclosed in U.S. Pat. No. 7,794,527. Alternatively, the detector 132 is a level sensor for detecting the drilling mud level into the tank 112.

The detector 132 is coupled with the level adjusting system 134 which is able to, according to an indicator given by the detector 132, adjust the elevation of the enclosure 62.

The gas-extraction device 52 according to the second and to the third embodiments of the disclosure allows maintaining the same volume of drilling mud inside the enclosure 62. This allows a constant volume of extracted gases to be sent to the gas analyzer 54. Indeed, with these configurations, there is no need to adjust manually the position of the gas trap so that the enclosure 62 is always immerged in drilling mud. Moreover, unlike the first embodiment, there is no need to use a pump upstream the enclosure as described above. As a consequence, the maintenance is even more reduced, so as the increase of the productivity and the safety of the drilling operation.

According to another embodiment of the gas-extraction device, not shown, the enclosure is fixed at the upper portion of the tank and the drilling mud level is maintained by the presence of a pump upstream the tank. By continuously feeding the tank, the drilling mud level remains constant since the tank comprises an overflow device. Then, the fixation height of the enclosure is adjusted according to the drilling mud level.

In a variant, the carrier gas is a pressurized neutral gas such as nitrogen and/or helium. It is stored for example in a pressurized gas enclosure such as a gas bottle.

FIG. 6 is a schematic functional diagram of a gas extraction device according to another embodiment of the disclosure.

The gas extraction device according to this embodiment comprises a gas-extraction device 152, that may be similar to any gas-extraction device 52 described hereinabove (such as the ones of FIG. 1 to 5). It comprises in particular an enclosure 162, a supply pipe 164 for supplying the drilling mud, a pipe 170 for introducing the carrier gas in the enclosure 162 and a gas extraction pipe 168 for transporting the carrier gas with gas extracted from the drilling fluid away from the enclosure 162.

Contrary to the embodiments of FIG. 2 to 5, the pipe 170 for introducing the carrier gas may introduce a carrier gas that is at the same pressure as the enclosure 162, for instance the atmospheric pressure. The pipe 170 may comprise an inlet opening outside, the carrier gas being air from the atmosphere surrounding the rigsite.

The gas extraction pipe 168 is connected to a gas analyzer 154 for analyzing the gas extracted from the drilling fluid in the enclosure 162. The gas analyzer 154 may be similar to the gas analyzer described hereinabove.

In this embodiment, the gas analyzer 154 is connected at its output to a flow regulator 204 such as a flow restrictor, in particular a sonic nozzle enabling to maintain a constant flow of gas exiting the enclosure 162 which is a mix of carrier gas and extracted gas. Downstream from the flow regulator 204, the gas-extraction device 152 also comprises a Venturi vacuum pump 202, forming a pressure controller.

The Venturi vacuum pump 202 comprises a main pipe 210 having an inlet 212 and an outlet 214 and a flow restrictor 216 between the inlet and the outlet separating the main pipe in a first upstream portion 217 and a second downstream portion 219. It also has an additional pipe 218 connecting the gas analyzer 154 via the flow regulator 204 to the main pipe 210, in the second portion 219. A gas is supplied in the Venturi vacuum pump 202 via the inlet 212 and when it passes the flow restrictor 216, due to the Venturi effect, its velocity increases while its pressure drops. The Venturi vacuum pump 202 is configured so that the pressure in the second portion 217 is below the pressure of the enclosure 162 and also below the pressure of the gas at the output of the flow regulator 204. For instance the gas introduced via the inlet 212 is at atmospheric pressure. It may however be extracted from a pressurized gas source or at any pressure value depending on the configuration of the vacuum pump.

In this embodiment, the gas coming from the additional pipe 218 is sucked in the Venturi vacuum pump 202, in view of the pressure difference, forming the flow that enables the circulation of the carrier gas and the extraction of the gas contained in the drilling fluid.

The Venturi vacuum pump 212 may be installed in the device at any other appropriate location, for instance upstream from the gas analyzer 154. However, installing it downstream from the gas analyzer 154 enables to avoid that the analyzed gas comprises gas coming from the Venturi vacuum pump inlet, therefore having a more accurate analysis.

The Venturi vacuum pump 202 may be configured to not include any moving parts and therefore necessitate only reduced maintenance.

The gas extraction device 152 according to the disclosure extracts gas with a regulated and steady flow even if there are inlet pressure variations at the inlet of the pressure controller. It may be installed easily at reduced costs in the field and only necessitates a reduced maintenance.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same purposes and/or achieving the same advantages of the embodiments introduced herein. A person having ordinary skill in the art should also realize that such equivalent constructions do not depart from the scope of the present disclosure, and that they may make various changes, substitutions and alterations herein without departing from the spirit and scope of the present disclosure.

The invention claimed is:

1. A gas extraction device for extracting at least one gas contained in a drilling mud, the device comprising:
    an enclosure,
    an equipment for supplying the drilling mud to the enclosure,
    an equipment for introducing a carrier gas into the enclosure,
    a gas analyzer for analyzing the gas, which is directly connected to the enclosure via a gas-extraction pipe of the gas-extraction device,
    wherein the device comprises a flow regulator able to regulate a flow rate of a gas flow containing at least carrier gas,
    and a venturi vacuum pump situated downstream of the enclosure and of the analyzer in relationship to a gas flow, wherein the venturi vacuum pump is configured for locally setting a pressure lower than the pressure of the enclosure, whereby the enclosure has a higher pressure than the venturi vacuum pump, wherein the flow regulator is interposed between the venturi vacuum pump and the enclosure.

2. The gas extraction device according to claim 1, wherein the gas analyzer comprises one of the following analyzers:
    a spectrometer, such as an infrared spectrometer, and/or
    a flame ionization detector chromatograph (FID), and/or
    a thermal conductivity detector chromatograph (TCD), and/or
    a gas chromatography system connected to a mass spectrometer (GC-MS).

3. The gas extraction device according to claim 1, wherein the flow regulator is a sonic nozzle.

4. The gas extraction device according to claim 1, wherein the gas extraction pipe has a length inferior to 10 meters.

5. The gas extraction device according to claim 1, wherein the gas analyzed at the gas analyzer does not include gas coming from the venturi vacuum pump.

6. The gas extraction device according to claim 1, wherein the means for introducing the carrier gas includes a pipe having an inlet opening outside to the atmosphere.

7. The gas extraction device according to claim 1, wherein the means for introducing the carrier gas is the only inlet for the carrier gas into the enclosure.

8. The gas extraction device according to claim 1, wherein the venturi vacuum pump includes an upstream portion and a downstream portion, and wherein the gas extraction pipe is connected to the upstream portion.

9. The gas extraction device according to claim 1, wherein the gas analyzer is connected at an outlet of the gas analyzer to the flow regulator.

10. The gas extraction device according to claim 1, wherein the gas-extraction pipe does not include a pump, a flow regulator, or a pump and a flow regulator.

11. The gas extraction device according to claim 1, comprising a tank for receiving the drilling mud, wherein the enclosure is positioned in the tank, and wherein the gas extraction device comprises a level control unit for regulating the level of the mud in the enclosure.

12. The gas extraction device according to claim 11, wherein the enclosure is positioned on an upper portion of the tank, and wherein the level control unit comprises a floating device, the floating device being able to float on the drilling mud, the floating device moving vertically upwards and downwards through a guiding equipment for guiding the floating device, the enclosure being mounted on the floating device.

13. The gas extraction device according to claim 11, wherein the level control unit comprises a detector able to detect a drilling mud level around the enclosure and a level adjusting system, coupled with the detector and configured to raise or to lower the enclosure according to an indicator given by the detector.

14. A method for extracting at least one gas contained in a drilling mud, the method comprising:
    providing a gas-extraction device according to claim 1,
    feeding the enclosure with drilling mud,
    providing carrier gas in the enclosure and forming a flow of carrier gas and gas extracted from the drilling mud situated in the enclosure with the venturi vacuum pump and the flow regulator,
    delivering the flow to the gas analyzer and analyzing the gas extracted from the drilling fluid with the gas analyzer, wherein delivering the flow to the gas analyzer includes delivering the flow without passing the flow through a vacuum pump or a flow regulator.

15. The method according to claim 14, wherein the gas analyzer is located in an explosive region of a drilling operation.

16. A gas extraction device for extracting at least one gas contained in a drilling mud, the device comprising:
    a tank for receiving the drilling mud, and an enclosure positioned in the tank,
    an equipment for supplying the drilling mud to the enclosure,
    an equipment for introducing a carrier gas into the enclosure,
    a level control unit for regulating a level of the mud in the enclosure, wherein the device comprises a sonic nozzle or capillary tube able to regulate a flow rate of a gas flow containing at least carrier gas, and a pressure controller situated downstream of the enclosure configured for locally setting a pressure lower than the pressure of the enclosure, wherein the sonic nozzle or capillary tube is interposed between the pressure controller and the enclosure.

17. The gas extraction device according to claim 16, wherein the enclosure is positioned on an upper portion of the tank, and wherein the level control unit comprises a floating device, the floating device being able to float on the drilling mud, the floating device moving vertically upwards and downwards through a guiding equipment for guiding the floating device, the enclosure being mounted on the floating device.

18. The gas extraction device according to claim 16, wherein the level control unit comprises a detector able to detect a drilling mud level around the enclosure and a level adjusting system, coupled with the detector and configured to raise or to lower the enclosure according to an indicator given by the detector.

19. The gas extraction device according to claim 16, wherein the sonic nozzle or capillary tube is configured to regulate at a constant flow rate by providing a constant outflow of gas based on a variable inflow of gas.

20. The gas extraction device according to claim 16, wherein the enclosure, the sonic nozzle or capillary tube, and the pressure controller lie on a fluid path from the enclosure to the pressure controller, and wherein the sonic nozzle or capillary tube is configured to regulate a flow of gas along an entirety of the fluid path at a constant flow rate.

* * * * *